United States Patent [19]
Knifton et al.

[11] Patent Number: 5,449,839
[45] Date of Patent: Sep. 12, 1995

[54] ONE STEP SYNTHESIS OF ETHYL T-BUTYL ETHER FROM T-BUTANOL USING β-ZEOLITE AND MULTIMETAL-MODIFIED β-ZEOLITE CATALYSTS

[75] Inventors: John F. Knifton, Austin; Pei-Shing E. Dai, Port Arthur, both of Tex.

[73] Assignee: Texaco Chemical Inc., White Plains, N.Y.

[21] Appl. No.: 279,057

[22] Filed: Jul. 22, 1994

Related U.S. Application Data

[63] Continuation of Ser. No. 57,373, May 6, 1993, abandoned.

[51] Int. Cl.⁶ .............................................. C07C 41/09
[52] U.S. Cl. ...................................................... 568/698
[58] Field of Search ........................................... 568/698

[56] References Cited

U.S. PATENT DOCUMENTS

| | | | |
|---|---|---|---|
| 4,714,787 | 12/1987 | Bell et al. | 568/697 |
| 4,918,244 | 4/1990 | Nelson et al. | 568/698 |
| 5,144,086 | 9/1992 | Harandi et al. | 568/698 |
| 5,162,592 | 11/1992 | Knifton et al. | 568/698 |

*Primary Examiner*—Johann Richter
*Assistant Examiner*—John Peabody
*Attorney, Agent, or Firm*—James L. Bailey; Kenneth R. Priem; Cynthia L. Hunter

[57] ABSTRACT

Disclosed is an improved process for preparing ethyl t-butyl ether in one step which comprises reacting tertiary butanol and ethanol in the presence of a catalyst selected from zeolite beta and zeolite beta modified with multimetals selected from the group consisting of Groups IB, VB, VIB, VIIB or VIII of the Periodic Table at a temperature of about 20° C. to 250° C. and atmospheric pressure to about 1000 psig, wherein when the temperature is in the operating range above about 140° C., the product comprises a two-phase mix of an ETBE-isobutylene and, optionally, diisobutylene product-rich phase and a heavier aqueous ethanol-rich phase.

9 Claims, No Drawings

ONE STEP SYNTHESIS OF ETHYL T-BUTYL ETHER FROM T-BUTANOL USING β-ZEOLITE AND MULTIMETAL-MODIFIED β-ZEOLITE CATALYSTS

This application is a continuation of application Ser. No. 08/057,373, filed May 6, 1993, now abandoned.

CROSS-REFERENCE

This application is related to pending U.S. Ser. No. 07/967,479, now abandoned. It is also related to U.S. Pat. Nos. 4,822,921; 4,827,048; 5,099,072; 5,081,318; 5,059,725; 5,157,162; 5,162,592; 5,157,161; 5,183,947; and allowed U.S. Ser. Nos. 07/917,218 now U.S. Pat. No. 5,217,218; 07/878,121 now U.S. Pat. No. 5,214,218; and 07/917,885 now U.S. Pat. No. 5,220,078, all of which are incorporated by reference herein in their entirety.

FIELD OF THE INVENTION

This invention concerns an improved process for preparing ethyl tertiary butyl ether (ETBE) in one step by the reaction of tertiary butanol and ethanol in the presence of a catalyst comprising a β-zeolite alone or modified with one or more metals selected from the group consisting of Groups IB, VB, VIB, VIIB and VIII of the Periodic Table as defined in the Condensed Chemical Dictionary, page 789. Metals which work well include transition metals found in Row 1 of Groups IB, VIB, VIIB, and VIII, particularly iron, copper, chromium, manganese, and nickel. The invention is especially advantageous in that the multimetal-modified zeolites exhibit both high activity during ethyl t-butyl ether synthesis from ethanol plus t-butanol and, additionally, allow for the cosynthesis of isobutylene and diisobutylene.

Generally, it is known that asymmetrical $C_4$–$C_7$ alkyl tertiary alkyl ethers are particularly useful as octane improvers for liquid fuels, especially gasoline. Methyl tertiary butyl ether (MTBE), ethyl t-butyl ether (ETBE), isopropyl t-butyl ether (IPTBE) and tertiary amyl methyl ether (TAME) are known to exhibit high octane properties. Much attention has been focused on production of these ethers due to the rapidly increasing demand for lead-free octane boosters for gasoline.

It is known in the art to produce ETBE or MTBE by reacting isobutylene with either ethanol or methanol, resulting in the formation of ETBE of MTBE, respectively. The reaction normally is conducted in liquid phase with relatively mild conditions. The isobutylene can be obtained from various sources, such as naphtha cracking, catalytic cracking, etc. The resulting reaction product stream contains the desired MTBE or ETBE, as well as unreacted isobutene and other $C_4$ hydrocarbons and methanol or ethanol.

Ethyl tertiary-butyl ether has long been recognized as a suitable blending cosolvent for hydrous ethanol in gasoline stocks. See U.S. Pat. No. 4,207,076. ETBE can be blended into a fuel gasoline at about a 10 to 20 volume percent level, usually nearer 9 to 12%, in which the fuel comprises about 70 to 84% gasoline and 5 to 20% of 95% ethanol, i.e. grain alcohol. ETBE solubilizes grain alcohol in gasoline in all proportions thereby allowing a wide latitude in the precise amount of ethanol which can be blended with gasoline.

There has previously been some interest in the use of ethyl-tertiary-butyl ether (ETBE) as a lead free octane booster for gasoline. Note, for example, the following publications: Iburra et al., "Getting the Lead Out With Ethyl t-Butyl Ether," CHEM TECH, Feb. 1988, pp. 120–122 and Verbanic, "ETBE: Ethanol's Motor Fuel Hope?" CHEMICAL BUSINESS, Oct. 1988, at pp. 38–39 and the paper presented at the DeWitt Petrochemical Review, Houston, Tex., Mar. 28–30, 1989, by Neerlich et al., entitled "Huels/UOP Technology for ETBE/MTBE Production." Recently, there has been increased interest in ETBE due to efforts in Washington, D.C., to extend tax credits for corn-based ethanol used to produce ETBE.

A number of U.S. patents and allowed U.S. applications assigned to Texaco Chemical Co. disclose methods of making alkyl tertiary alkyl ethers, including ETBE, in one step.

In U.S. Pat. No. 4,822,921, to Texaco Chemical Co., there is described a method for preparing alkyl tertiary alkyl ethers, including ETBE, which comprises reacting a $C_1$–$C_6$ primary alcohol with a $C_4$–$C_{10}$ tertiary alcohol over a catalyst comprising an inert support impregnated with phosphoric acid.

U.S. Pat. No. 4,827,048, to Texaco Chemical Co., describes a method for preparing alkyl tertiary alkyl ethers from the same reactants using a heteropoly acid on an inert support.

U.S. Pat. No. 5,099,072, to Texaco Chemical Co., discloses a method for preparing alkyl tertiary alkyl ethers, including ETBE, over an acidic montmorillonite clay catalyst which possesses very specific physical parameters.

U.S. Pat. No. 5,081,318, to Texaco Chemical Co., discloses a method for preparing alkyl tertiary alkyl ethers by reacting a $C_1$–$C_6$ primary alcohol with a $C_4$–$C_{10}$ tertiary alcohol over a catalyst comprising a fluorosulfonic acid-modified zeolite.

U.S. Pat. No. 5,059,725, to Texaco Chemical Co., discloses a method for preparing alkyl tertiary alkyl ether, including ethyl tertiary butyl ether, from $C_1$–$C_6$ primary alcohols and $C_4$–$C_{10}$ tertiary alcohols over a catalyst comprising ammonium sulfate or sulfuric acid on a Group IV oxide.

U.S. Pat. No. 5,157,162, to Texaco Chemical Co., discloses a fluorosulfonic acid-modified clay catalyst for the production of, ETBE, inter alia, from $C_1$–$C_6$ primary alcohols and $C_4$–$C_{10}$ tertiary alcohols.

In U.S. Pat. No. 5,162,592, to Texaco Chemical Co. there is described a method for producing alkyl tertiary alkyl ethers from $C_1$–$C_6$ primary alcohols and $C_4$–$C_{10}$ tertiary alcohols using a multimetal-modified catalyst.

A hydrogen fluoride-modified montmorillonite clay catalyst is employed in U.S. Pat. No. 5,157,161, to Texaco Chemical Co., to produce alkyl tertiary alkyl ethers, including ETBE.

In U.S. Pat. No. 5,183,947, to Texaco Chemical Co., fluorophosphoric acid-modified clays are employed as catalysts in a method to produce alkyl tertiary alkyl ethers.

In allowed U.S. Ser. No. 07/917,218, assigned to Texaco Chemical Co., there is disclosed the use of a super acid alumina or a faujasite-type zeolite to produce alkyl tertiary alkyl ethers.

Allowed U.S. Ser. No. 07/878,121, to Texaco Chemical Co., discloses the use of a haloacid-modified montmorillonite clay catalyst to convert $C_1$–$C_6$ primary alcohols and $C_4$–$C_{10}$ tertiary alcohols to alkyl tertiary alkyl ethers.

Fluorophosphoric acid-modified zeolites are employed in allowed U.S. Ser. No. 07/917,885, to Texaco Chemical Co., to produce alkyl tertiary alkyl ethers.

Other references in the art which disclose ETBE as a product usually require two stages rather than one and use isobutylene as a reactant.

For example, in U.S. Pat. No. 4,334,890, a mixed $C_4$ stream containing isobutylene is reacted with aqueous ethanol to form a mixture of ethyl tertiary butyl ether (ETBE) and tertiary butyl alcohol (TBA).

U.S. Pat. No. 5,015,783 describes a process for producing ethers, including ETBE which comprises passing a feed stream to an etherification zone, passing the etherification zone effluent stream to a distillation column and further involves cooling the overhead stream, refluxing and recycling.

A process for the production of ETBE and/or MTBE is disclosed in U.S. Pat. No. 2,480,940.

U.S. patents which discuss the production of ETBE as well as MTBE include:

U.S. Pat. No. 5,070,016
U.S. Pat. No. 4,440,063
U.S. Pat. No. 4,962,239
U.S. Pat. No. 4,015,783

These patents all use isobutylene as the coreactant rather than t-butanol.

The use of zeolites for certain reactions is known in the art. Beta-zeolite was first synthesized at Mobil R and D labs and exhibited improved thermal and acid stability over previously synthesized zeolites.

J. B. Higgins, et al. of Mobil Research and Development published an article in ZEOLITES, 1988, Vol. 8, November, 446–452 titled "The Framework Topology of Zeolite Beta." In the article Higgins et al. disclose what is known about the framework topology of zeolite beta. The information has been determined using a combination of model building, distance-least-square refinement and powder pattern simulation.

In an article titled "Cumene Disproportionation over Zeolite $\beta$ I. Comparison of Catalytic Performances and Reaction Mechanisms of Zeolites," Applied Catalysis, 77 (1991) 199–207, Tseng-Chang Tsai, Chin-Lan Ay and Ikai Wang disclose a study demonstrating that cumene disproportionation can be applied as a probe reaction for zeolite structure. It is revealed that zeolite beta would have application potential in the production of diisopropylbenzene for reasons of activity, selectivity and stability.

In a second part of the article by Tsai et al., "II. Stability Enhancement with Silica Deposition and Steam Pretreatment", Ibid, pp. 209–222, Tsai and Wang disclose their development of two methods to improve the stability of zeolite beta, silica deposition and steam pretreatment.

E. Bourgeat-Lami et al. have published an article discussing their study of the effects of calcination of as synthesized or ammonium-exchanged forms of Zeolite Beta. See "Stability of the Tetrahedral Aluminum Sites in Zeolite Beta," E. Bourgeat et al., Catalysis Letters, 1990, 5, p. 265. These researchers came to the conclusion that the tetrahedral aluminum sites disappearing upon calcination can be readily restored by a simple treatment in ammonium nitrate. The parent sample of $\beta$-zeolite with a Si/Al ratio of 16.9 was synthesized at 130° C. using tetraethylammonium hydroxide as template. The NMR spectrum indicated a dealumination corresponding to about 25%. When this material was treated with ammonium nitrate solution, washed and over dried at 70° C., the signal of octahedral aluminum was no longer detected while that at 53 ppm narrowed and increased to 95% of its original value.

Patents in the art which employ zeolite beta relate mainly to dewaxing, and cracking of hydrocarbon feedstock.

An article titled "Beta Zeolite as Catalyst or Catalyst Additive for the Production of Olefins During Cracking or Gas Oil," was written by L. Bonetto et al., 9th International Zeolite Conference, July 1992, FP 22. The authors note that with the greater demand for oxygenated compounds there is indication there might be increased demands for catalysts and conditions which maximize $C_3$, $C_4$ and $C_5$ olefins. They suggest that $\beta$-zeolite could be used alone or combined with Y-zeolite as a suitable zeolite component. Various catalysts were studied with respect to minimization of diffusional requirements and zeolite stability.

U.S. Pat. No. 4,419,220, to Mobil, discloses a process for dewaxing a hydrocarbon feedstock containing straight chain paraffins which comprises contacting the feedstock with a zeolite beta catalyst having a Si:Al ratio of at least 30:1 and a hydrogenation component under isomerization conditions.

Another European Application to Mobil, EPO 0 094 82, discloses simultaneous catalytic hydrocracking and hydrodewaxing of hydrocarbon oils with zeolite beta.

In European Patent Application 0 095 303, to Mobil, there is a disclosure of dewaxing distillate fuel oils by the use of zeolite beta catalysts which, preferably have a silica:alumina ratio over 100:1. Ratios as high as 250:1 and 500:1 are disclosed as useful.

Another U.S. Pat. No. 4,518,485, to Mobil, discloses a process for dewaxing a hydrocarbon feedstock containing paraffins selected from the group of normal paraffins and slightly branched paraffins and sulfur and nitrogen compounds where, after conventionally hydrotreating the feedstock to remove sulfur and nitrogen, the hydrotreated feedstock is dewaxed by contacting the feedstock with a catalyst comprising zeolite beta having a silica/alumina ratio of at least 30:1.

In U.S. Pat. No. 4,740,292, to Mobil, there is disclosed a catalytic cracking process which comprises cracking a hydrocarbon feed in the absence of added hydrogen with a cracking catalyst comprising a zeolite beta component and a faujasite component comprising at least one crystalline aluminosilicate of the faujasite structure, the weight ratio of the faujasite component to the zeolite beta component being from 1:25 to 20:1.

Large pore $\beta$-zeolite has been employed in the synthesis of industrially important para-cymene by toluene isopropylation. See "Toluene Isopropylation over Zeolite $\beta$ and Metallosilicates of MFI Structure," P. A. Parikh et al., Applied Catalysis, A, 1992, 90, p. 1.

From available art, there do not appear to be methods available, except those referred to by reference, assigned to Texaco Chemical Co., for adapting a catalyst to produce ethyl tertiary butyl ether in high yields in one step by reacting ethanol instead of methanol with tertiary butanol.

It would be a valuable advance in the art if a method were available for the synthesis of ethyl tertiary butyl ether employing one step technology and a catalyst exhibiting extended life which accommodates the use of various grades of ethanol, i.e. denatured, grain and pure with tertiary butanol, rather than isobutylene. The co-synthesis of isobutylene and diisobutylene using the crude feedstock reactants would make such a process even more attractive.

SUMMARY OF THE INVENTION

In accordance with certain of its aspects, the novel method of this invention for preparing ethyl tert-butyl ether (ETBE) from tertiary butyl alcohol and ethanol in one-step comprises reacting tertiary butyl alcohol and ethanol in the presence of a catalyst comprising $\beta$-zeolite or multimetal-modified $\beta$-zeolite at an elevated temperature and moderate pressure.

DESCRIPTION OF THE INVENTION

Preparation of the product of this invention may be carried out typically by reacting tertiary butyl alcohol and ethanol in the presence of an etherification catalyst. The etherification is carried out in one-step and the catalyst preferably comprises a $\beta$-zeolite or a $\beta$-zeolite modified with one or more metals selected from the group consisting of Group IB, VB, VIB, VIIB or VIII of the Periodic Table.

The reaction can be represented by the following:

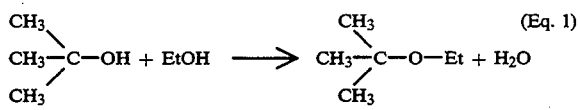

(Eq. 1)

Generally the ethanol and t-butanol coreactants may be mixed in any proportion in order to generate the desired ethyl t-butyl ether (ETBE), but preferably the molar ratio of ethanol to t-butanol (tBA) in the feed mixture should be between 10:1 and 1:10, if the yield of desired ETBE is to be maximized. In order to achieve maximum selectivity to ETBE, and optimum conversion per pass, an excess of ethanol in the liquid feed is desirable. The most preferred ethanol-to-tertiary butanol molar ratio is from 1:1 to 5:1.

In certain circumstances, it may be particularly desirable that the tBA conversion be high enough (e.g. 70% or greater), such that the crude product mix phase separates into an isobutylene-ETBE product-rich phase and a heavier aqueous ethanol phase. Optionally the ETBE-isobutylene phase will also contain diisobutylene. Preferably such a product phase separation would be achieved at as low an etherification temperature as possible, but it is particularly observed in the range 140°–200° C.

The synthesis of Eq. 1 can also be conducted where the t-butanol and ethanol reactants are mixed with certain other components including water, ketones such as acetone ($Ac_2O$) and methyl ethyl ketone (MEK), peroxides and hydroperoxides such as di-t-butyl peroxide (DTBP) and allyl t-butyl peroxide (ATBP), and t-butyl hydroperoxide (TBHP), as well as esters such as t-butyl formate (TBF). Typically each of said classes of components makes up less than 10% of the total feed mixture.

It has been discovered in the instant invention that the $\beta$-zeolites and the multimetal-modified zeolite beta catalysts herein disclosed function to exhibit concurrent quantitative decomposition of peroxide in the alcohol feedstock in addition to converting tertiary butanol plus ethanol to ETBE. This constitutes an important advantage in a commercial setting.

The instant one-step process may also be applied to the preparation of other alkyl tertiary alkyl ethers. For example, said process may be applied to the reaction of a $C_1$–$C_6$ primary alcohol such as methanol, ethanol, n-propanol and n-hexanol with a $C_4$–$C_{10}$ tertiary alcohol such as, for example, tertiary butanol and tertiary amyl alcohol. Reaction of methanol with t-butanol would yield methyl tert-butyl ether (MTBE), while reaction of methanol with tertiary amyl alcohol (2-methyl-2-butanol) would then yield methyl tertiary amyl ether (TAME). Alternatively a mixture of alcohols, e.g., a mixture of $C_1$–$C_5$ alcohols, could be reacted to give a mixture of alkyl tert-alkyl ethers.

In the modified catalyst of the instant invention good results were realized using certain crystalline aluminosilicate zeolites as catalysts for the reaction represented in Eq. 1. Particularly effective were the isostructural group of $\beta$-zeolites.

Zeolite beta was first synthesized at the Mobil Research and Development Laboratories. It exhibited improved thermal and acid stability over previously synthesized zeolites, Higgins et al., supra, p. 446.

The composition of zeolite beta is described in U.S. Pat. Nos. 3,308,069; 4,419,220; 4,518,485 and 4,740,292. In those references, zeolite beta is typically described as follows:

Zeolite beta is a crystalline aluminosilicate having a pore size greater than 5 Angstroms. The composition of the zeolite, as described in U.S. Pat. No. 3,308,069, in its as synthesized form may be expressed as follows:

where X is less than 1, preferably less than 0.7; TEA represents the tetraethylammonium ion; Y is greater than 5 but less than 100; and W is up to about 60 (it has been found that the degree of hydration may be higher than originally determined, where W was defined as being up to 4), depending on the degree of hydration and the metal cation present. The TEA component is calculated by differences from the analyzed value of sodium and the theoretical cation to structural aluminum ratio of unity.

As discussed in the J. B. Higgins, et al. reference, Supra, p. 446, the first clues to the crystal structure of zeolite beta were evidenced from chemical and physical property measurements. Ion-exchange isotherms of Na-$\beta$ at 25° C. indicated that cations as large as tetraethylammonium (TEA+) exchanged completely into the pore system. This behavior suggests that beta contains at least 12-membered rings opening into channels, because TEA+ is too large to exchange through 10-membered rings such as those in ZSM-5. The complete exchange of cations in beta indicated the presence of channels instead of cages, because it is not possible to remove all the cations from cage structures such as Na faujasite. Additional evidence was obtained from organic sorption data and density measurements. Cyclohexane sorption of 14.6–19.4 wt % and a measured density of 1.61 g/cm$^3$ ruled out undimensional pore systems such as those in ZSM-12, ZSM-22, ZSM-23 and ZSM-48. Structural similarities among beta, mordenite and ZSM-12 were suspected because all three may be synthesized in Na+—TEA+ systems from highly siliceous batch compositions. Further, zeolite beta is easily synthesized in the $SiO_2/Al_2O_3$ range of 30–50. This lies between TEA+ mordenite (typically 10–30) and ZSM-12 (typically, >60), suggesting the beta framework contains large fractions of both 4- and 5-membered rings.

In the Tsai and Wang reference, Supra, part II, p. 209, stability enhancement is discussed. Two methods, silica deposition and steam pretreatment, have been developed to substantially improve zeolite beta stability.

At comparable conversion levels, the alpha value decreases from 0.23 for unmodified zeolite beta to 0.09 after mild steam pretreatment. Where zeolite beta is steam pretreated, apparently acid strength of the zeolite is enhanced and the yield of aromatics is increased, Ibid, p. 213.

Where silica is deposited on the zeolite beta, the pore openings are narrowed and the selectivity for para-diisopropyl benzene is enhanced. On p. 215, Ibid, it is stated that maximum stabilization was obtained around 0.10 g $SiO_2$ $g_{cat}^{-1}$. According to this reference the activity of zeolite beta completely disappeared at a silica deposition of 0.21 g $SiO_2$ $g_{2cat}^{-1}$. It is stated that the best stability enhancement with silica deposition, obtaining an alpha value of 0.08, is less significant than that with steam pretreatment, wherein a value of 0.01 is obtained, however the excellent disproportionation selectivity of zeolite beta is little affected by silica deposition.

Ibid, p. 215, it is stated that zeolite beta has two types of three dimensional pore openings, the linear and the tortuous channel. The former has pore openings of 7.5 Å × 5.7 Å and the latter has pore openings of 6.5 Å × 5.6 Å. When silica, for example, is deposited on zeolite beta, the pore opening was narrowed or blocked by the deposited silica. It was concluded that silica deposition selectively removes strong acid sites and increases the population of medium acid sites.

In the fully base-exchanged form, zeolite beta has the composition:

$$[(X/n)M(1\pm0.1-X)H]AlO_2 \cdot YSiO_2 \cdot WH_2O$$

where X, Y and W have the values listed above and n is the valence of the metal M. This form of the zeolite may be converted partly to the hydrogen form by calcination, e.g. at 200° C. to 900° C. or higher. The completely hydrogen form may be made by ammonium exchange followed by calcination in air or an inert atmosphere such as nitrogen, see U.S. Pat. No. 4,419,220.

Zeolite beta is characterized by the following X-ray diffraction pattern:

d Values of Reflection in zeolite beta
11.40±0.2
7.40±0.2
6.70±0.2
4.25±0.1
3.97±0.1
3.00±0.1
2.20±0.1

The preferred forms of zeolite beta are the highly acidic, high silica forms, having silica-to-alumina mole ratio of at least 10:1, and preferably in the range of 10:1 to 50:1 in the as-synthesized form. A narrower range of 20:1 to 30:1 is preferred and the zeolite beta powders demonstrated in the examples possess $SiO_2/Al_2O_3$ ratios of about 23:1 to 26:1. It has been found, in fact, that zeolite beta may be prepared with silica-to-alumina mole ratios above the 200:1 maximum specified in U.S. Pat. Nos. 3,308,069 and these forms of the zeolite may perform well in the process. Ratios of 50:1, or even higher, may be used where available.

The silica-to-alumina ratios referred to in this specification are the structural or framework ratios, that is, the ratio of the $SiO_4$ to the $AlO_4$ tetrahedra, which together constitute the structure of which the zeolite is composed. It should be understood that this ratio may vary from the silica-to-alumina ratio determined by various physical and chemical methods. For example, a gross chemical analysis may include aluminum which is present in the form of cations associated with the acidic sites on the zeolite, thereby giving a low silica-to-alumina ratio. Similarly, if the ratio is determined by the thermogravimetric analysis (TGA) of ammonia desorption, a low ammonia titration may be obtained if cationic aluminum prevents exchange of the ammonium ions onto the acidic sites. These disparities are particularly troublesome when certain treatments, such as the dealuminization method described below which result in the presence of ionic aluminum free of the zeolite structure, are employed. Due care should therefore be taken to ensure that the framework silica-to-alumina ratio is correctly determined.

The silica-to-alumina ratio of the zeolite may be determined by the nature of the starting materials used in its preparation and their quantities relative one to another. Some variation in the ratio may therefore be obtained by changing the relative concentration of the silica precursor relative to the alumina precursor, but definite limits in the maximum obtainable silica-to-alumina ratio of the zeolite need be observed. For zeolite beta, this limit is usually about 100:1 (although higher ratios may be obtained) and for ratios above this value, other methods are usually necessary for preparing the desired high silica zeolite. This method generally comprises contacting the zeolite with an acid, preferably a mineral acid such as hydrochloric acid. The dealuminization proceeds readily at ambient and mildly elevated temperatures and occurs with minimal losses in crystallinity to form high silica forms of zeolite beta with silica-to-alumina ratios of at least 100:1, with ratios of 200:1 or even higher being readily attainable.

Particularly effective in the subject synthesis of ETBE are the $\beta$-zeolites modified with multiple metals.

Illustrative of suitable $\beta$-zeolites for the practice of this invention include Valfor C806$\beta$, Valfor CP815$\beta$ and Valfor C861. Valfor ® is the registered trademark of the PQ Corporation. Valfor ® C806$\beta$ zeolite is zeolite beta powder in template cation form. It is a high silica shape selective zeolite which contains the organic template used in the crystallization step, having been isolated after filtration and washing of the synthesis product. C806$\beta$ has a $SiO_2/Al_2O_3$ molar ratio of 23–26; the crystal size is 0.1–0.7 um; the surface area after calcination is about 700–750 m²/g; the cyclohexane adsorption capacity after calcination is 19–24 g/100 g; $Na_2O$ content is about 0.01–1.0% by weight anhydrous; and, the organic content is about 11–13% by weight, on a water-free basis.

Valfor ® C815$\beta$ zeolite is a calcined zeolite beta powder in hydrogen, sodium form. It is similar to C806$\beta$ except the product has been calcined to decompose the organic template. C815$\beta$ is a high silica, shape selective aluminosilicate with a large pore diameter. C815$\beta$ also has a $SiO_2/Al_2O_3$ molar ratio of about 23–26; the crystal size, surface area, cyclohexane adsorption capacity and $Na_2O$ are all within the same ranges as given for C806$\beta$, Valfor ® C861$\beta$ is an extrudate made of 80% C815$\beta$ powder and 20% alumina powder.

The metals useful for modifying the zeolite in the instant invention comprise those from Group IB, VB, VIB, VIIB and VIII of the Periodic Table, including said transition metals. Preferred metals are those found in Row 1 of Groups IB, VIB and VIII of the Periodic Table and include copper, chromium, manganese, iron and nickel. Especially good results were observed using combinations of iron, manganese and chromium or combinations of nickel, copper and chromium, on VALFOR® Zeolite 861β.

Said zeolites are preferably impregnated with said specified metals as their salts, particularly their metal nitrate or chloride salts, in an aqueous, alcoholic, or ketonic media over a period of 1–24 hours, then the solids are filtered off, dried at elevated temperature, e.g. 120° C., for a period of time and calcined at 300°–800° C. for a further period, e.g. 315° C. for 2 hours, followed by 540° C. for another 2 hours.

Examples 1 demonstrates the preparation of the multimetal-modified catalysts. Salts of iron, chromium and manganese, such as their chlorides or nitrates, in anhydrous or hydrated forms were dissolved in water, alcohol, or acetone and the β-zeolites were added, most often, in the form of extrudates. The catalysts were then calcined by heating to 300° to 800° C. and optionally reduced in a stream of hydrogen at 200° C.

The amount of the various metals deposited on the zeolite can vary. The amount of each individual metal, i.e., iron, chromium, copper, manganese, and nickel, can vary from 0.01 to 10.0%. Where iron, chromium and manganese are deposited on 861β the preferred weight percent is from 0.1% to 5.0%.

Said catalysts may be in the form of powders, pellets, granules, spheres, shapes and extrudates. The examples described herein demonstrate the advantages of using extrudates.

The reaction may be carried out in either a stirred slurry reactor or in a fixed bed continuous flow reactor. The catalyst concentration should be sufficient to provide the desired catalytic effect. Said catalysts may be formed in the presence of a binder, such as Group III or Group IV oxide, including alumina or silica. Said binders may comprise 10% to 90% of the formed catalyst.

Etherification can generally be conducted at temperatures from 20° to 250° C.; the preferred range is 80° to 200° C. Good results are observed throughout this temperature range. However, it can be noted that the best conversion figures for DTBP and tert-butanol are observed when the temperature is around 140° C. or higher. The total operating pressure may be from 0 to 1000 psig, or higher. The preferred pressure range is 50 to 500 psig.

Typically, ETBE is generated continuously in up to ca. 50 wt % concentration or greater in the crude liquid product at total liquid hourly space velocities (LHSV) of up to 6 or higher and relatively mild conditions, where:

$$LHSV = \frac{\text{Volume Of Total Liquid Feed Run Through The Reactor Per Hour}}{\text{Volume of Catalyst In Reactor}}$$

Conversions of t-butanol (tBA, wt %) are estimated in the following examples using the equation:

$$\frac{(\text{Mole \% of } tBA \text{ in Feed} - \text{Mole \% of } tBA \text{ in Product})}{\text{Mole \% of } tBA \text{ in Feed}} \times 100$$

The examples which follow illustrate the one-step synthesis of ETBE from tBA and EtOH (Eq. 1) using β-zeolites or multimetal-modified β-zeolites particularly in the form of extrudates.

In particular, the accompanying examples illustrate:
1) The cosynthesis of ETBE, isobutylene ($C_4H_8$) and diisobutylene ($C_8H_{16}$) in Example 2 from t-butanol (tBA) plus ethanol via etherification, dehydration and dimerization reactions using an iron, chromium, manganese-modified β-zeolite prepared by the method of Example 1. Here tBA conversion levels are typically 66% at 120° C. and product phase separation is realized at temperatures of 160° C. or above.
2) In Example 3, the cosynthesis of ETBE, isobutylene and diisobutylene from tBA/EtOH is illustrated using β-zeolite where tBA conversions are 71% at 120° C. and 97% at 180° C. Again product phase separation into an ETBE, isobutylene and, optional diisobutylene-rich phase and a heavier aqueous ethanol phase is realized at 140° C.
3) Example 4 illustrates the cosynthesis of ETBE and isobutylene via ethanol/t-butanol etherification using a crude feedstock also containing sizeable quantities of water, isopropanol (2-PrOH), acetone ($Ac_2O$) and methyl ethyl ketone (MEK). An extended catalyst life with this feed has been demonstrated.

The examples are only intended as a means of illustration and it is understood the invention is not meant to be limited thereby.

EXAMPLE 1

This example illustrates the preparation of a multimetal-modified β-zeolite.

To 102 g of β-zeolite (Valfor C861β, 80% β-zeolite, 20% alumina) in 1/16" diameter extruded form was added a solution of ferric chloride hydrate (1.04 g), chromium(III) nitrate, hydrate (1.64 g) and manganese(II) nitrate hydrate (1.10 g) in 92 cc of distilled water. Impregnation of the β-zeolite was allowed to occur over 1–2 hours, then the solids were filtered off, dried at 120° C. overnight, and calcined at 315° C. for 2 hours, followed by 540° C. for another 2 hours.

The recovered green solid extrudates showed the presence of:
% Fe=0.27
% Cr=0.19
% Mn=0.08
Acidity=0.35 meq/g

EXAMPLE 2

This example illustrates the production of ethyl t-butyl ether from t-butanol and ethanol using the Fe, Cr, Mn-impregnated β-zeolite of Example 1.

Synthesis was conducted in a tubular reactor (½" i.d., 12" long) constructed of 316 stainless steel, operated upflow and mounted in a furnace, controllable to ±1.0° C. and fitted with pumps allowing flow control to <±1 cc/hr. The reactor was also fitted with a pressure regulating device and equipment for monitoring temperature, pressure and flow rate.

The reactor was charged at the beginning of the experiment with 25 cc of a Fe, Cr, Mn-treated β-zeolite, prepared by the procedure of Example 1, as 1/16" diameter extrudates. A glass wall screen was placed at the top and bottom of the reactor to ensure the catalyst would remain in the middle portion. The catalyst bed was treated with an ethanol/t-butanol (1.1:1 molar mix) upflow, at a rate of 50 cc/hr, while the reactor was held at 120° C., with a total pressure of 300 psi. Samples of crude product effluent were collected periodically on stream, in 316 ss bombs and analyzed by glc.

Typical analyses data for samples taken under these conditions are summarized in Table 1. Concentrations of ETBE, isobutylene, diisobutylene ($C_8H_{16}$), diethyl ether (DEE), ethanol, and t-butanol in the reaction effluent were also measured at a series of higher temperatures (140°–160° C.). These data are also included in Table 1.

For Sample #1, at 120° C.:
  tBA Conversion = 66%
  ETBE Selectivity = 58%
  Isobutylene Selectivity = 28%
  Diisobutylene Selectivity = 12%
For Sample #5, at 160° C.:
  tBA Conversion = 89%

EXAMPLE 3

Using the equipment and following the procedures of Example 2, a β-zeolite catalyst (C861β from PQ Corp., 80% Beta, 20% alumina) was treated with 1.1:1 molar mix of ethanol and t-butanol at a series of operating temperatures from 120° to 180° C. Concentrations of ETBE, isobutylene, diisobutylene, diethyl ether, ethanol and t-butanol in the product effluents, under the specified conditions, as determined by glc, are summarized in the accompanying Table 2.

Of particular note:
For Sample #2, at 120° C.
  tBA Conversion = 71%
  ETBE Selectivity = 46%
  Isobutylene Selectivity = 24%
  Diisobutylene Selectivity = 26%

TABLE 1

| Ex. | Catalyst | EtOH/tBA Molar Ratio | Feed Rate (cc/hr) | Temp. (°C.) | Time On Stream (Days) | ETBE Sample | PRODUCT COMPOSITION (WT %) METHOD 26 | | | | | METHOD 32 | |
|---|---|---|---|---|---|---|---|---|---|---|---|---|---|
| | | | | | | | $H_2O$ | EtOH | $C_4H_8$ | tBA | ETBE | $C_8H_{16}$ | DEE |
| 2 | Ex. 1[a] | 1.1:1 | 50 | | | FS-1 | | 40.6 | | 58.9 | | | |
| | | | | 120 | 1 | →1 | 8.2 | 27.6 | 8.3 | 19.9 | 31.0 | 7.3 | 0.04 |
| | | | | | | 2 | 8.1 | 27.5 | 8.2 | 20.6 | 30.3 | 7.1 | 0.03 |
| | | | | 140 | 2 | 3 | 11.5 | 36.6 | 8.0 | 13.0 | 18.4 | 17.8 | 0.23 |
| | | | | | | 4 | 11.0 | 35.4 | 8.9 | 12.2 | 19.5 | 17.2 | 0.22 |
| | | | | 160 | 3 | →5[b] | 1.6 | 14.7 | 17.9 | 4.6 | 17.8 | 51.6 | 1.4 |
| | | | | | | | 19.8 | 55.0 | 3.1 | 8.8 | 6.8 | 6.1 | 1.0 |
| | | | | | | 6[c] | 1.9 | 18.7 | 15.9 | 4.1 | 17.0 | 51.5 | 1.3 |
| | | | | | | | 20.2 | 54.6 | 3.5 | 8.5 | 6.8 | 6.6 | 1.1 |

[a] 0.2% Fe, 0.2% Cr, 0.2% Mn on Valfor C861β
[b] Relative sizes of phases, 1.05:1 (t:b)
[c] Relative sizes of phases, 1.04:1 (t:b)

For Sample #8, at 180° C.:
  tBA Conversion = 97%

TABLE 2

| Ex. | Catalyst | EtOH/tBA Molar Ratio | Feed Rate (cc/hr) | Temp. (°C.) | Time On Stream (Days) | ETBE Sample | PRODUCT COMPOSITION (WT %) METHOD 26 | | | | | METHOD 32 | |
|---|---|---|---|---|---|---|---|---|---|---|---|---|---|
| | | | | | | | $H_2O$ | EtOH | $C_4H_8$ | tBA | ETBE | $C_8H_{16}$ | DEE |
| 3 | C861β | 1.1:1 | 50 | | | FS-1 | | 40.2 | | 59.2 | | | |
| | | | | 120 | 1 | 1 | 9.2 | 30.5 | 7.4 | 17.4 | 26.1 | 16.7 | 0.04 |
| | | | | | | →2 | 8.9 | 29.8 | 7.7 | 16.9 | 27.1 | 16.7 | 0.04 |
| | | | | 140 | 2 | 3[b] | a | | | | | a | |
| | | | | | | | 16.7 | 49.3 | 3.8 | 10.9 | 10.9 | 13.0 | 0.5 |
| | | | | | | 4[c] | 2.7 | 22.1 | 12.8 | 21.2 | 21.2 | 49.4 | 0.4 |
| | | | | | | | 16.2 | 49.7 | 3.9 | 10.8 | 10.8 | 9.9 | 0.9 |
| | | | | 160 | 3 | 5[d] | 1.1 | 13.0 | 15.6 | 2.0 | 10.4 | 60.6 | 2.3 |
| | | | | | | | 23.5 | 61.7 | 1.3 | 5.1 | 3.1 | 4.5 | 1.7 |
| | | | | | | 6[e] | 1.1 | 12.8 | 15.5 | 2.2 | 10.5 | 59.2 | 2.0 |
| | | | | | | | 23.5 | 59.7 | 1.5 | 5.5 | 3.4 | 5.2 | 1.6 |
| | | | | 180 | 4 | 7[f] | 0.7 | 10.4 | 34.0 | 1.1 | 4.6 | 49.0 | 2.4 |
| | | | | | | | 28.9 | 59.8 | 2.8 | 2.5 | 1.3 | 3.4 | 2.0 |
| | | | | | | 8[g] | 0.7 | 10.6 | 34.2 | 1.0 | 4.5 | 38.8 | 1.9 |
| | | | | | | | 26.1 | 60.4 | 3.7 | 2.4 | 1.4 | 3.2 | 1.7 |

[a] Insufficient quantity for analysis
[b] Relative phase sizes 0.73:1 (t:b)
[c] Relative phase sizes 1.31:1 (t:b)
[d] Relative phase sizes 1.18:1 (t:b)
[e] Relative phase sizes 1.09:1 (t:b)
[f] Relative phase sizes 1.56:1 (t:b)
[g] Relative phase sizes 1.45:1 (t:b)

EXAMPLE 4

Using the equipment and following the procedures of Example 2, a sample of β-zeolite catalyst (80% Beta, 20% alumina) was treated with a crude 1.5:1 molar mix of ethanol and t-butanol feedstock that also contains significant quantities of water, isopropanol (2-PrOH), acetone and methyl ethyl ketone. Etherification was conducted at 120° C., 300 psi, using a LHSV of 2.

Concentrations of each of these components, plus isobutylene, diisobutylene, diethyl ether and ETBE, in the product effluents was determined by glc. Typical data are given in the accompanying Table 3. Over the period of the experiment (>1000 hours), there was essentially no change in catalyst activity as measured by the level of t-butanol conversion. Typical calculated conversion data are as follows:

| Sample | 1 | 3 | 8 |
|---|---|---|---|
| Time on Stream (Days): | 1 | 13 | 43 |
| t-Butanol Conv. | 62 | 62 | 61 |

C. and a pressure of about atmospheric to about 1000 psig to obtain ethyl tert-butyl ether product, wherein the product exhibits phase separation at 160° C.

2. The method of claim 1 wherein the zeolite beta has a crystal size in the range of 0.1–0.7 um.

3. The method of claim 1 wherein the zeolite beta has a surface area, after calcination, of 700–750 $m^2g$.

4. The method of claim 1 wherein the zeolite beta exhibits a cyclohexane adsorption capacity after calcination of 19–24 g/100 g.

5. The method of claim 1 wherein the zeolite beta contains $Na_2O$ 0.01%–1.0% by weight anhydrous.

6. The method of claim 1 wherein the zeolite beta is characterized by the following X-ray diffraction pattern:

d Values of Reflections in Zeolite Beta
11.40±0.2
7.40±0.2
6.70±0.2
4.25±0.1
3.97±0.1
3.00±0.1
2.20±0.1.

TABLE 3

| Ex. | Catalyst | Feed Rate (cc/hr) | Temp. (°C.) | Time On Stream (Days) | Sample | PRODUCT COMPOSITION (WT %) | | | | | | | | | |
|---|---|---|---|---|---|---|---|---|---|---|---|---|---|---|---|
| | | | | | | METHOD 26 | | | | | | | METHOD 32 | | |
| | | | | | | $H_2O$ | EtOH | $C_4H_8$ | MEK | tBA | ETBE | $Ac_2O$ | 2-PrOH | $C_8H_{16}$ | DEE |
| 4 | C861β | 50 | | | FS-1 | 4.8 | 42.4 | | 1.5 | 45.9 | | 0.3 | 5.2 | | |
| | | | 120 | 1 | →1 | 10.4 | 32.5 | 5.8 | 1.5 | 17.5 | 23.0 | 0.3 | 5.9 | 5.5 | 0.03 |
| | | | | 8 | 2 | 10.0 | 31.0 | 6.5 | 1.6 | 16.9 | 24.5 | 0.3 | 6.0 | 5.7 | |
| | | | | | FS-2 | 4.7 | 42.6 | | 1.5 | 45.8 | | 0.3 | 4.8 | | |
| | | | | 13 | →3 | 9.9 | 31.3 | 6.2 | 1.5 | 17.4 | 25.1 | 0.3 | 5.2 | 4.8 | |
| | | | | 22 | 4 | 9.9 | 31.6 | 6.5 | 1.5 | 17.5 | 24.3 | 0.3 | 5.7 | 4.8 | |
| | | | | | FS-3 | 4.7 | 42.4 | | 1.5 | 45.7 | | 0.3 | 5.2 | 0.1 | |
| | | | | 31 | 5 | 10.5 | 32.1 | 6.1 | 1.4 | 18.7 | 23.1 | 0.3 | 5.7 | 4.1 | |
| | | | | | FS-4 | 4.8 | 42.4 | | 1.5 | 45.6 | | 0.3 | 5.2 | | |
| | | | | 37 | 6 | 9.9 | 31.8 | 6.4 | 1.5 | 18.5 | 24.2 | 0.3 | 5.1 | 3.8 | |
| | | | | 42 | 7 | 9.8 | 31.1 | 6.4 | 1.5 | 18.1 | 25.4 | 0.3 | 5.2 | 3.6 | |
| | | | | | FS-5 | 4.7 | 42.7 | | 1.5 | 45.7 | | 0.3 | 5.2 | | |
| | | | | 43 | →8 | 9.8 | 31.2 | 6.8 | 1.5 | 17.9 | 25.4 | 0.3 | 5.3 | 3.2 | |

What is claimed is:

1. A method for synthesizing ethyl tertiary-butyl ether which comprises reacting t-butanol with ethanol in the presence of a catalyst consisting essentially of zeolite beta having a silica:alumina ratio of 23–26 formed in the presence of a Group III oxide, modified with one or more metals selected from the group consisting of iron, chromium and manganese, and continuously contacting said ethanol and t-butanol in a molar amount of from about 10:1 to 1:10 over said zeolite catalyst at a temperature of about 80° C. to about 200°

7. The method of claim 1 wherein the concentrations of metals modifying said zeolite may vary from 0.01% to 10.0% for each metal.

8. The method of claim 7, wherein the concentrations of metals modifying said zeolite beta may vary from 0.1 wt % to 5.0 wt %.

9. The method of claim 1 wherein the Group III oxide is alumina comprises 10% to 90% of the formed catalyst.

* * * * *

UNITED STATES PATENT AND TRADEMARK OFFICE
CERTIFICATE OF CORRECTION

PATENT NO. : 5,449,839
DATED : September 12, 1995
INVENTOR(S) : John F. Knifton, Pei-Shing E. Dai It is certified that error appears in the above-indentified patent and that said Letters Patent is hereby corrected as shown below:

In Col. 14, line 49, after "alumina" insert -- and --.

Signed and Sealed this

Twenty-sixth Day of December, 1995

Attest:

BRUCE LEHMAN

*Attesting Officer*  *Commissioner of Patents and Trademarks*